(12) United States Patent
Jadhav et al.

(10) Patent No.: US 12,734,293 B2
(45) Date of Patent: Sep. 15, 2026

(54) PRESSURE-REGULATING AND ADJUSTING CONNECTOR FOR INFUSION

(71) Applicant: CareFusion 303, Inc., San Diego, CA (US)

(72) Inventors: Amarsinh Deeliprao Jadhav, Bangalore (IN); Kanjimpuredathil Muralikrishna Menon, Bangalore (IN); Abin Austin, Thrissur (IN); Rahul Malviya, British Columbia (CA); Praveen Nalawade, Bengaluru (IN)

(73) Assignee: CAREFUSION 303, INC., San Diego, CA (US)

( * ) Notice: Subject to any disclaimer, the term of this patent is extended or adjusted under 35 U.S.C. 154(b) by 1071 days.

(21) Appl. No.: 17/707,490

(22) Filed: Mar. 29, 2022

(65) Prior Publication Data

US 2022/0313904 A1 Oct. 6, 2022

Related U.S. Application Data

(60) Provisional application No. 63/168,180, filed on Mar. 30, 2021.

(51) Int. Cl.
*A61M 5/168* (2006.01)
*A61M 5/315* (2006.01)

(52) U.S. Cl.
CPC .... *A61M 5/16804* (2013.01); *A61M 5/31595* (2013.01); *A61M 2205/3334* (2013.01)

(58) Field of Classification Search
CPC .............. A61M 5/484; A61M 5/31595; A61M 5/16813; A61M 5/16881; A61M 39/24;
(Continued)

(56) References Cited

U.S. PATENT DOCUMENTS 2,896,662 A * 7/1959 Thomas ................ F16K 11/065 137/538
3,643,685 A * 2/1972 Hays ....................... F16K 1/126 251/340
(Continued)

FOREIGN PATENT DOCUMENTS

WO WO-2013116670 A1 8/2013

OTHER PUBLICATIONS

Queensland Department of Health, "Peripheral intravenous catheter (PIVC) Guideline", Queensland Health, 2012, retrieved from the internet at https://www.health.qld.gov.au/_data/assets/pdf_file/0025/444490/icare-pivc-guideline.pdf.
(Continued)

*Primary Examiner* — Wesley G Harris
*Assistant Examiner* — Charles W Nichols
(74) *Attorney, Agent, or Firm* — MASCHOFF BRENNAN

(57) ABSTRACT

A connector for coupling a container carrying a medical fluid to a vascular access device may include a housing comprising and inner surface defining an internal chamber comprising a fluid channel disposed in the internal chamber. The fluid channel may include a pair of oppositely positioned cutouts. The connector may further include a slider disposed and supported in the internal chamber and having an internal compartment and an aperture through inner walls of the internal compartment. The slider may be reciprocally movable between (i) a first position, where the aperture of the slider is axially aligned with the pair of cutouts to allow the medical fluid to flow through the outlet, and (ii) a second position where the aperture of the slider is not aligned with the pair of cutouts and the inner walls of the slider blocks fluid connection between the slider and the fluid channel.

26 Claims, 6 Drawing Sheets

(58) Field of Classification Search
CPC .... A61M 2039/242; A61M 2039/2413; A61M 2039/2433; A61M 2039/2473; A61M 2205/334; Y10T 137/7791; Y10T 137/7834; F16K 17/22; F16K 31/445; F16K 15/145
USPC .......................................... 251/340, 346, 351
See application file for complete search history.

(56) References Cited

U.S. PATENT DOCUMENTS

| | | | | |
|---|---|---|---|---|
| 3,985,156 | A * | 10/1976 | Walker .................... | F17C 13/04 251/351 |
| 4,863,429 | A | 9/1989 | Baldwin | |
| 5,322,511 | A | 6/1994 | Armbruster et al. | |
| 5,379,797 | A * | 1/1995 | Rogers .................... | F16K 17/22 137/503 |
| 6,945,954 | B2 | 9/2005 | Hochman et al. | |
| 7,401,751 | B2 * | 7/2008 | Holder ................... | G05D 7/014 244/129.5 |
| 9,089,682 | B2 * | 7/2015 | Yeh ....................... | A61M 39/24 |
| 10,269,266 | B2 | 4/2019 | Rios et al. | |
| 2005/0049556 | A1 | 3/2005 | Tanaka | |
| 2010/0179488 | A1 * | 7/2010 | Spiegel ........... | A61M 25/10182 73/729.1 |
| 2010/0217209 | A1 | 8/2010 | Meng et al. | |
| 2012/0029479 | A1 * | 2/2012 | Kraushaar ........... | A61M 39/105 604/533 |
| 2018/0318504 | A1 * | 11/2018 | Capdevila ......... | A61M 5/16881 |

OTHER PUBLICATIONS

International Search Report and Written Opinion for Application No. PCT/US2022/021389, dated Jul. 7, 2022, 15 pages.

Australian Office Action for Application No. 2022246767, dated Jul. 28, 2025, 3 pages.

European Office Action for Application No. 22715894.6, dated Dec. 12, 2025, 5 pages.

Japanese Office Action for Application No. 2023-560180, dated Nov. 26, 2025, 7 pages including machine translation.

Indian Office Action for Application No. 202317065116, dated Jun. 8, 2026, 7 pages.

Japanese Office Action for Application No. 2023-560180, dated Jun. 5, 2026, 3 pages including translation.

* cited by examiner 110
120
112
125
145
133
130
152
154
135
159
155
50
139
156
157

PRESSURE-REGULATING AND ADJUSTING CONNECTOR FOR INFUSION

REFERENCE TO RELATED APPLICATIONS

This application clauses priority to U.S. Provisional Application No. 63/168,180, filed Mar. 30, 2021, the entire disclosure of which application being incorporated herein by this reference.

TECHNICAL FIELD

The present disclosure generally relates to a connector for connecting a medical container, such as a syringe, to a vascular access device for infusion injection of a medical fluid to a patient, and particularly to pressure-regulating connector for connecting a medical container, such as a syringe, to a vascular access device for infusion injection of a medical fluid at safe infusion pressures.

BACKGROUND

In general, vascular access devices are inserted into veins via peripheral or central vessels. Vascular access devices can be used for infusing fluid (e.g., saline solution, blood, medicaments, and/or total parenteral nutrition) into a patient, withdrawing fluids (e.g., blood) from a patient, and/or monitoring various parameters of the patient's vascular system.

However, vascular access devices can become occluded. To ensure vascular access devices are used properly and do not become occluded, standards of practice have been developed. These standards include a cleaning procedure, which is commonly referred to as a flush procedure. These flush procedures maintain the patency of the vascular access device.

Flush procedures may be enhanced by use of a syringe specifically designed to generate lower injection pressure, such as for instance a 10 mL-diameter syringe barrel, or by use of a "push-pause" or pulsatile flushing technique to remove debris or residue in the catheter that may cause occlusion or other undesirable effects.

However, fast injection of flush fluid into peripheral IV lines leads to transient pressure build-up within the vein where the catheter is sited. This pressure may lead to vein damage (rupture or collapse) and infusate infiltration/extravasation, causing clinical complications and the need to replace the peripheral IV catheter.

The description provided in the background section should not be assumed to be prior art merely because it is mentioned in or associated with the background section. The background section may include information that describes one or more aspects of the subject technology.

SUMMARY

There is therefore a need for a device for delivering a flushing injection pressure that stays below predetermined threshold in order to avoid damage to blood vessels.

In accordance with various embodiments of the present disclosure, a connector for connecting a container containing a medical fluid to a vascular access device may include a housing having a proximal end, a distal end defining an outlet, and an inner surface defining an internal chamber comprising a fluid channel disposed in the internal chamber, and a slider disposed and supported in the internal chamber, and sleeved over the fluid channel. The fluid channel may extend from the proximal end to the distal end, and may include a pair of oppositely positioned cutouts along a length thereof. The slider may include an internal compartment and an aperture through inner walls of the internal compartment. The slider may be reciprocally movable between (i) a first position, where the aperture of the slider at least partially overlaps with the pair of cutouts to allow the medical fluid to flow through the outlet, and (ii) a second position where the aperture of the slider is not aligned with the pair of cutouts and the inner walls of the slider block fluid connection between the slider and the fluid channel. The slider may be movable to the first position when the medical fluid applies a fluid pressure less than or equal to a predetermined threshold, and the slider may be movable to the second position when the medical fluid applies a fluid pressure greater than the predetermined threshold.

In accordance with various embodiments of the present disclosure, a connector for connecting a container containing a medical fluid to a vascular access device may include a housing having a proximal end, a distal end defining an outlet, and an inner surface defining an internal chamber comprising a fluid channel disposed in the internal chamber, and a slider disposed and supported in the internal chamber and sleeved over the fluid channel. The fluid channel may extend from the proximal end to the distal end, and may include an inner surface defining a lumen of the fluid channel. The inner surface may have a threaded profile extending at least partially along the inner surface. The slider may be reciprocally movable between (i) an open position when the medical fluid applies a fluid pressure less than or equal to a predetermined threshold, and where the slider is fluidly coupled to the fluid channel to allow the medical fluid to flow along the threaded profile to the outlet, and (ii) a closed position when the medical fluid applies a fluid pressure greater than the predetermined threshold, and where fluid connection between the slider and the fluid channel is blocked.

In accordance with various embodiments of the present disclosure, a connector for connecting a container containing a medical fluid to a vascular access device may include a housing comprising a proximal end, a distal end defining an outlet, and an inner surface defining an internal chamber comprising a fluid channel disposed in the internal chamber. The fluid channel may extend from the proximal end to the distal end, and the housing further may further include an opening extending through the inner and outer surfaces thereof. The connector may further include a pressure adjuster mounted in the internal chamber and rotatably actuatable via the opening to adjust a pressure of the medical fluid, and a slider disposed and supported in the internal chamber and sleeved over the fluid channel. The slider may be reciprocally movable between (i) an open position when the medical fluid applies a fluid pressure less than or equal to a predetermined threshold, and where the slider is fluidly coupled to the fluid channel to allow the medical fluid to flow to the outlet, and (ii) a closed position when the medical fluid applies a fluid pressure greater than the predetermined threshold, and where fluid connection between the slider and the fluid channel is blocked.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The following figures are included to illustrate certain aspects of the embodiments and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figures 1, 2:
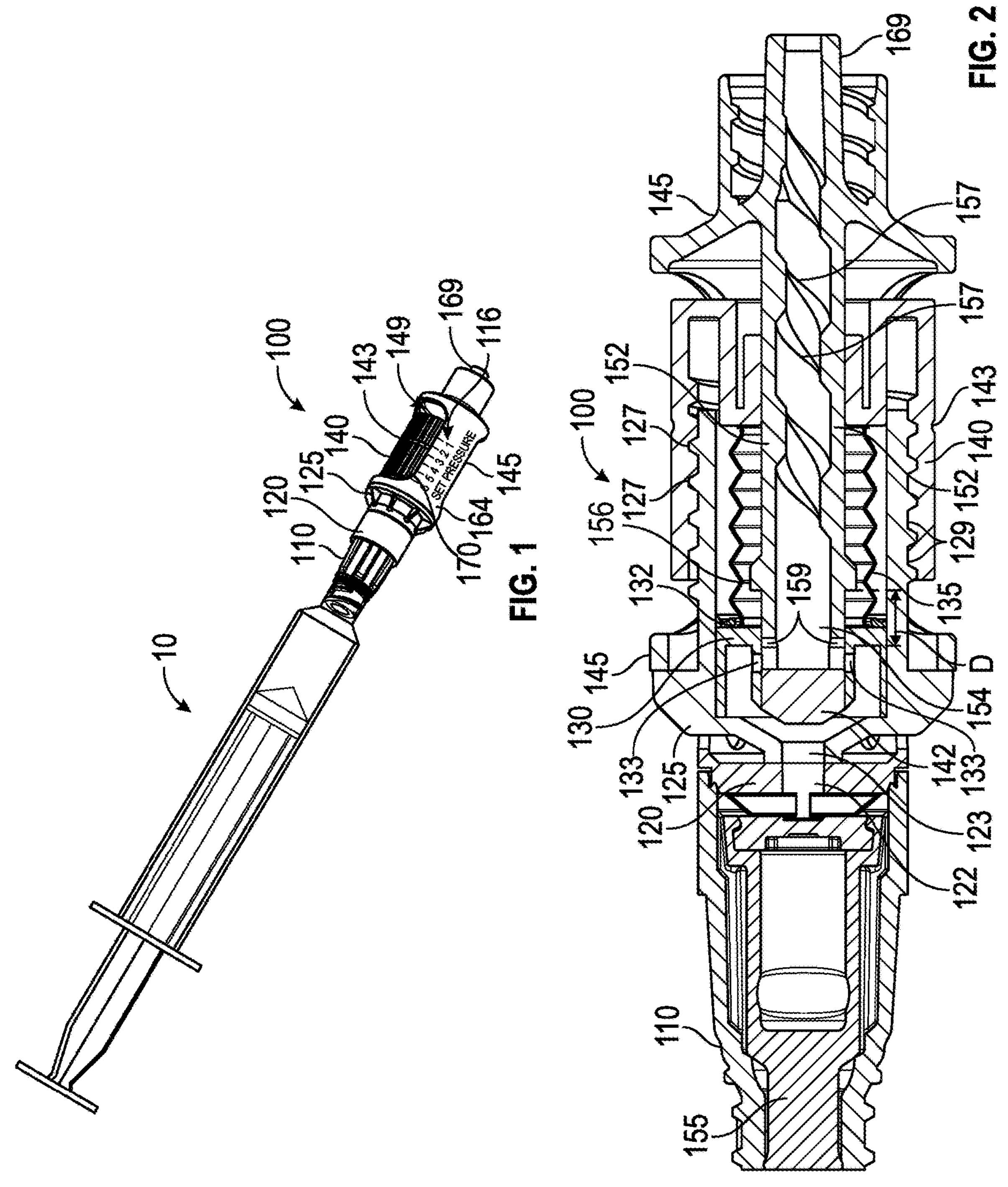
FIG. 1 illustrates an isometric view of a pressure-regulating connector coupled to a syringe, in accordance with some embodiments of the present disclosure.
FIG. 2 illustrates a cross-sectional view of the pressure-regulating connector, in accordance with some embodiments of the present disclosure.

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Rapid injection of flush fluid into peripheral IV lines leads to transient pressure build-up within the vein where the catheter is sited. This pressure frequently leads to vein damage (rupture or collapse) and infusate infiltration/extravasation, causing clinical complications and the need to replace the catheter.

Flushing is an essential strategy in maintaining patency of a vascular access device. Current flushing methods include employing devices specifically configured to deliver a low infusion pressure (e.g., a 10 milliliter (mL) diameter syringe barrel), and/or to implement a pulsatile flushing technique (also referred to as a push-pause drug infusion). For example, in vitro studies have shown that 10 short boluses of 1 mL interrupted by brief pauses may be more effective at removing solid deposits as compared to continuous low-flow techniques.

Various embodiments of the present disclosure are directed to providing a pressure-regulating connector capable of delivering a fluid at a flushing injection pressure within a predetermined pressure range (e.g., a pressure less than vein rupture pressure, but greater than or equal to generic flushing pressure). Various embodiments of the present disclosure are additionally directed to providing a pressure-regulating connector configured to allow the user to adjust the infusion pressure based on specific patient needs. Additionally, various embodiments of the present disclosure are directed to providing a pressure-regulating connector configured to create flow turbulence in the outlet channel in order to replace the conventional push-pause pulsatile flushing technique.

For example, various embodiments of the present disclosure provide a pressure control mechanism integrated with a needleless valve connector, thereby eliminating the need for additional components, and potentially providing a cost savings. Further, the pressure-regulating connectors and systems of the various embodiments described herein with integrated pressure adjuster allow the user to adjust infusion pressure according to individual or customized patient health conditions. Additionally, the pressure-regulating connectors and systems of the various embodiments described herein may maintain safe infusion pressure by regulating the flow with a reciprocating slider assembly. Furthermore, the pressure-regulating connectors and systems of the various embodiments described herein include a fluid channel with inner surface having threaded profile—which creates turbulent flow—thereby eliminating the need for the push-pause techniques applied by currently existing connectors.

FIG. 1 illustrates an isometric view of a pressure-regulating connector 100 fluidly coupled to a syringe 10, in accordance with some embodiments of the present disclosure. FIG. 2 illustrates a cross-sectional view of the pressure-regulating connector 100, in accordance with some embodiments of the present disclosure. As depicted in FIG. 1, in some embodiments, the pressure-regulating connector 100 may be configured to connect a medical container 10, such as prefilled or pre-fillable syringe to a vascular access device, such as an IV (intravenous) catheter, such that the medical fluid contained in the syringe 10 passes through the pressure-regulating connector 100 before reaching the vascular access device.

Referring to FIGS. 1 and 2, the pressure-regulating connector 100 may include a housing 145 defining an internal chamber 149 having an internal fluid channel 152 for circulation of the medical fluid through the connector 100 from a needleless connector 110 to a fluid outlet 169 of the housing 145. In some embodiments, the needleless connector 110 may be coupled to the syringe 10, through which the medical fluid may be delivered to the fluid outlet 169 of the pressure-regulating connector 100, via the needleless connector 110. In other embodiments, the needleless connector 110 may be coupled to an extension set (e.g., an IV extension set (not shown)) through which the medical fluid may be delivered to the fluid outlet 169 via the needleless connector 110.

Figures 3, 4:
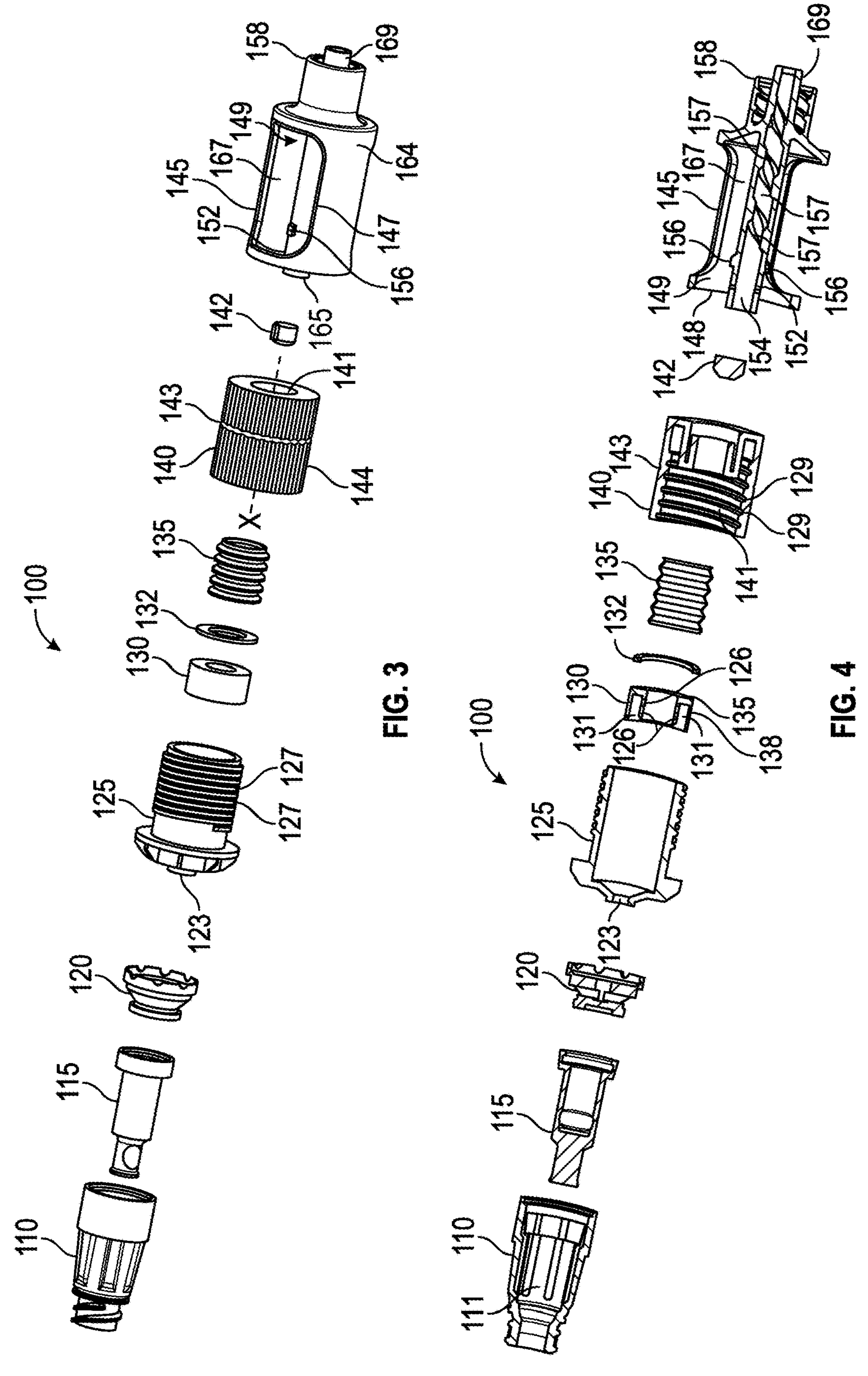
FIG. 3 illustrates an exploded perspective view of the pressure-regulating connector of FIG. 1, in accordance with some embodiments of the present disclosure.
FIG. 4 illustrates an exploded cross-sectional view of the pressure-regulating connector of FIG. 2, in accordance with some embodiments of the present disclosure.

FIG. 3 illustrates an exploded perspective view of the pressure-regulating connector of FIG. 1, in accordance with some embodiments of the present disclosure. FIG. 4 illustrates an exploded cross-sectional view of the pressure-regulating connector of FIG. 2, in accordance with some embodiments of the present disclosure. As depicted in FIGS. 3 and 4, with continued reference to FIGS. 1 and 2, the housing 145 may include a proximal end 148, a distal end 158, and an inner surface 167 defining an internal chamber 149. As depicted, the internal chamber 149 may include a fluid channel 152 disposed in the internal chamber 149. The fluid channel 152 may extend from the proximal end 148 to the distal end 158 of the housing 145. A proximal end of the fluid channel 152 may define an opening 165, and a distal end of the fluid channel 152 may define an outlet port 169 of the housing 145. In some embodiments, the fluid channel 152 may further include a pair of oppositely positioned cutouts 159 along a length thereof. An end cap 142 may be positioned over the opening 165 such that fluid flowing into the housing 145 from the needleless connector 110 may bypass the opening 165, and instead enter the fluid channel 152 via the pair of oppositely positioned cutouts 159.

Referring back to FIG. 2 with continued reference to FIGS. 3 and 4, the pressure-regulating connector 100 may further include a slider 130 disposed and supported in the internal chamber 149. For example, in some embodiments, a resilient member 135 may be mounted over the fluid channel 152 and coupled distally to the slider 130 to support the slider 130 within the internal chamber 149. The resilient member 135 may be in the form of bellows or any similar spring components. As depicted in FIG. 2, the slider 130 may be sleeved over the end cap 142 and the fluid channel 152 and supported at a base or distal end thereof by the resilient member 135.

In some embodiments, the slider 130 may have inner walls 126, an outer wall 138, and an internal compartment 131 defined between the inner and outer walls 126 and 138 of the slider 130. The slider 130 may further include an aperture 133 through the inner walls 126. For example, as depicted, the aperture 133 may be in the form of a pair of apertures 133 positioned through opposing inner walls 126.

Figures 5A, 5B:
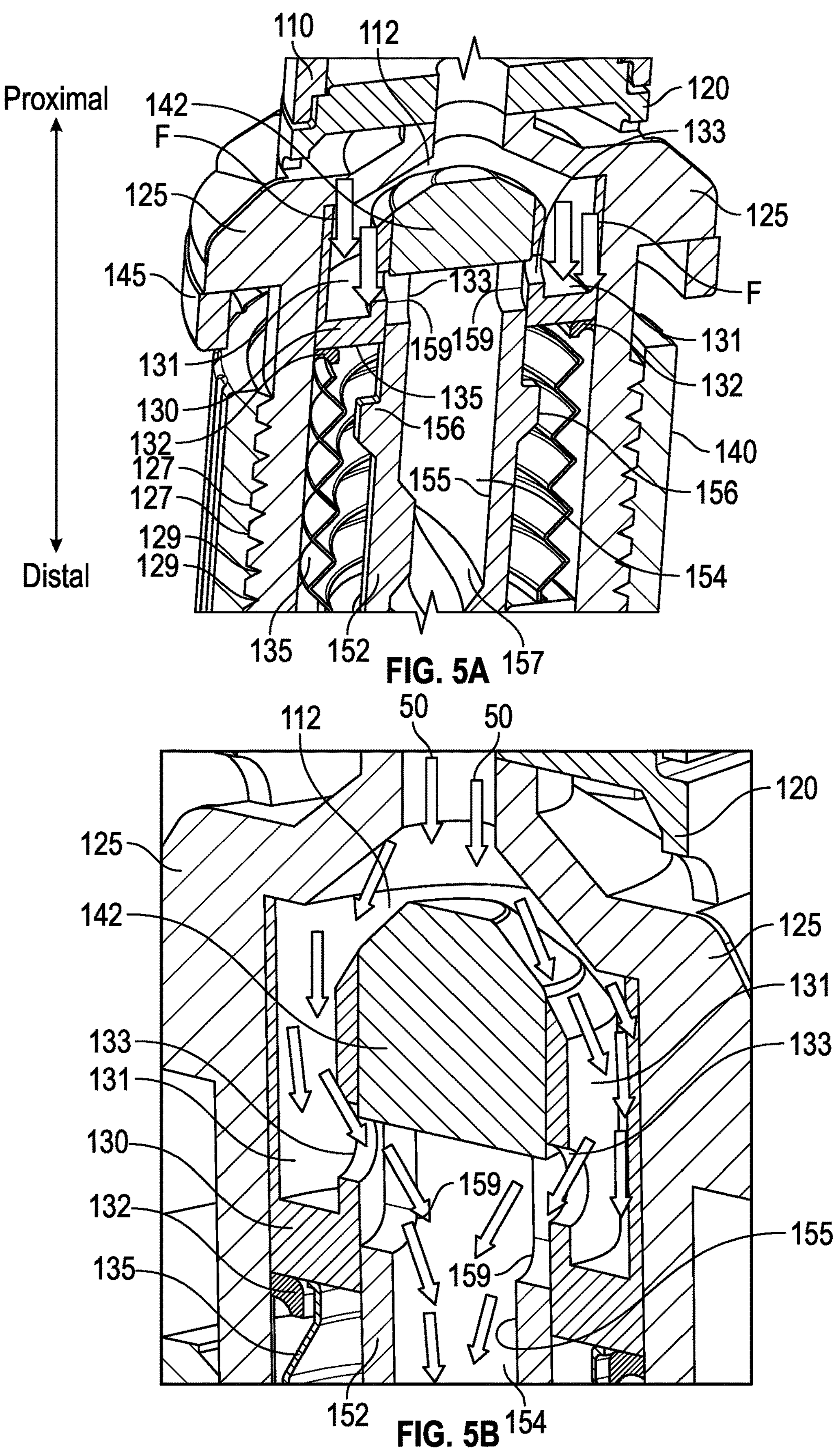
FIG. 5A illustrates a partial cross-sectional view of the pressure-regulating connector including slider subject to a fluid pressure, in accordance with some embodiments of the present disclosure.
FIG. 5B illustrates a partial cross-sectional view of the pressure-regulating connector including slider subject to a fluid pressure in an open position when the medical fluid pressure is less than or equal to a predetermined threshold, in accordance with some embodiments of the present disclosure.

FIG. 5A illustrates a partial cross-sectional view of the pressure-regulating connector including slider subject to a fluid pressure, in accordance with some embodiments of the present disclosure. FIG. 5B illustrates a partial cross-sectional view of the pressure-regulating connector including slider subject to a fluid pressure in an open position when the medical fluid pressure is less than or equal to a predetermined threshold, in accordance with some embodiments of the present disclosure. As illustrated in FIG. 5A, when a distal fluid pressure is exerted on the slider 130 (arrows F on FIG. 5A), the distal pressure exerts the force F on a floor of the internal compartment 131 of the slider 130 and pushes the slider 130 distally to the position illustrated in FIG. 5B, thereby compressing the resilient member 135. As shall be described in further detail below, when the medical fluid flows into the housing 145 and applies a fluid pressure to the slider 130 which is less than or equal to a predetermined threshold pressure, the slider 130 may be displaced or otherwise moved distally along the length of the fluid channel 152 towards a first or open position, illustrated for example in FIG. 5B. For example, the resilient member 135 may compress to allow the slider 130 to be displaced a first distance to the first or open position when the medical fluid applies the fluid pressure that is less than or equal to the predetermined threshold. In the open position, the pair of apertures 133 of the slider 130 may be axially aligned or at least partially overlap with the pair of cutouts 159 of the fluid channel 152 to allow the medical fluid 50 to flow through the outlet port 169 (illustrated in FIG. 2) via the internal compartment 131 and the fluid channel 152. In some embodiments, the pressure-regulating connector 100 may further include a seal 132 disposed at the base or distal end of the slider 130 surrounding the fluid channel 152 to prevent leakage of the medical fluid between the slider 130 and the fluid channel 152. For example, the seal 132 may be a low friction seal which causes limited to no inhibiting of the reciprocating motion of the slider 130. In some embodiments, the seal 132 may be a low friction lip seal.

Figures 6A, 6B:
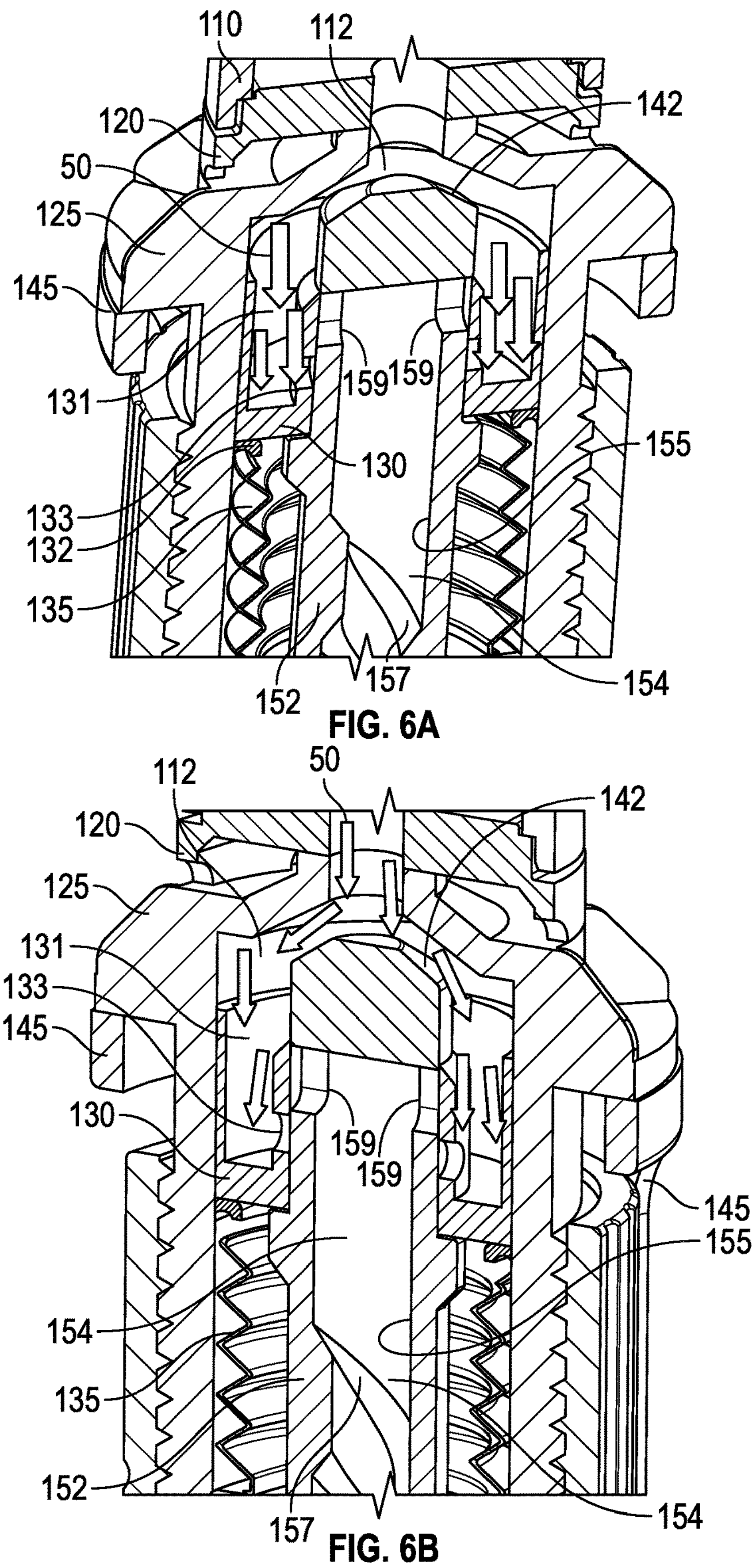
FIG. 6A illustrates a partial cross-sectional view of the pressure-regulating connector including slider subject to a medical fluid pressure, in accordance with some embodiments of the present disclosure.
FIG. 6B illustrates a partial cross-sectional view of the pressure-regulating connector including slider subject to a medical fluid pressure in a closed position when the medical fluid applies a fluid pressure greater than the predetermined threshold, in accordance with some embodiments of the present disclosure.

As shall be further described below, when the medical fluid continues to flow into the housing 145 and applies a fluid pressure that is greater than the predetermined threshold pressure to the slider 130, the slider 130 may be further displaced or otherwise moved distally along the length of the fluid channel 152 towards a second or closed position, illustrated for example in FIG. 6B. For example, the resilient member 135 may further compress to allow the slider 130 to be displaced a second distance to the second or closed position when the medical fluid applies the fluid pressure that is greater than the predetermined threshold. As depicted in FIG. 5A, the fluid channel 152 may further include a stop 156 protruding radially outward from an outer surface of the fluid channel 152 to prevent the slider 130 from moving further distally past the second or closed position. In the closed position, the pair of apertures 133 of the slider 130 may not be aligned or may not otherwise overlap with the pair of cutouts 159 such that the inner walls 126 of the slider block fluid communication between the slider 130 and the fluid channel 152. Accordingly, the medical fluid having the fluid pressure above the threshold safe amount is trapped inside the slider 130 and cannot flow into the vascular access device via the fluid channel 152. As such, infusion pressure of the medical fluid to the vascular access device may be maintained at or below safe infusion pressures, thereby advantageously preventing issues commonly occurring with currently existing infusion connectors. For example, an issue commonly associated with infusion procedures is that rapid injection of flush fluid into peripheral IV lines leads to transient pressure build-up within the patient's vein where the catheter is inserted. This pressure frequently leads to vein damage (rupture or collapse) and infusate infiltration/extravasation, causing complications and the need to replace the PIV catheter. Since the pressure-regulating connector of the various embodiments described herein maintains the infusion pressure of the medical fluid to the vascular access device at or below safe infusion pressures, the aforementioned issues commonly occurring with currently existing infusion connectors are minimized or altogether eliminated. The pressure-regulating connector of the various embodiments described herein is advantageously capable of delivering flushing injection pressure within a predetermined pressure range that is less than vein rupture pressure.

According to various embodiments of the present disclosure, the pressure-regulating connector 100 may further include a cover 125 coupled to the housing 145 and surrounding the slider 130, the fluid channel 152 and the resilient member 135. As depicted, a needleless connector 110 including a deformable or compressible valve member 115 may be mounted to the cover 125 and fluidly coupled to the slider 130. For example, in some embodiments, the needleless connector 110 may include a base plate 120 defining an outlet port 122 of the needleless valve 110. The cover 125 may further define an inlet port 123 at a proximal end thereof. As depicted, the outlet port of the needleless connector 110 and the inlet port 123 of the cover 125 may fluidly communicate a fluid chamber 111 of the needleless valve 110 with the internal compartment 131 of the slider for delivery of the medical fluid to the vascular access device when the fluid pressure is below or equal to the predetermined threshold pressure. In some embodiments, the cover may include a plurality of engagement features 127 on an outer surface thereof. For example, the cover 125 may include a plurality of threads 127.

Referring back to FIG. 1, with continued reference to FIGS. 3 and 4, the pressure-regulating connector 100 may further include a pressure adjuster 140 rotatably mounted in the internal chamber 149 and sleeved over the fluid channel 152. For example, as illustrated, the pressure adjuster may be in the form of a cylindrical body having an inner surface 141 and an outer surface 144. In some embodiments, the inner surface 141 of the pressure adjuster 140 may include a plurality of engagement features 129. For example, as depicted in FIG. 4, the inner surface 141 of the pressure adjuster 140 may include a plurality of threads 129.

In some embodiments, the housing 45 may further include an opening 147 extending through the inner and outer surfaces 167 and 164 of the housing 145 and fluidly communicating the internal chamber 149 with an exterior of the housing 145. Accordingly, the pressure adjuster 140 may be accessed via the opening 147 and manipulated to rotate about a central longitudinal axis X thereof to adjust the fluid pressure. For example, in some embodiments, in an assembled configuration of the pressure adjuster 140 and the cover 125, the plurality of engagement features or threads 129 of the pressure adjuster 140 and the plurality of engagement features or threads 127 of the cover may engage and interconnect so as to allow the pressure adjuster 140 to rotate and translate relative to the cover 125 within the internal chamber 149.

As depicted in FIG. 1, in some embodiments, the outer surface 164 of the housing 145 may include a plurality of graduations 116. For example, the graduations 116 may indicate a set pressure of the medical fluid flowing through the pressure adjustment connector 100. As further depicted, the pressure adjuster 140 may further include an indicator 143 disposed around at least a portion of the outer surface of the pressure adjuster 140. For example, in some embodiments, the indicator 143 may be in the form of a line of a desired color. Accordingly, when the pressure adjuster 140 is actuated or otherwise rotated to adjust and/or set the fluid pressure, rotational engagement and interconnection between the plurality of engagement features 129 and 127 of the respective pressure adjuster 140 and cover 125 allows the pressure adjuster 140 to be rotated about the axis X and translated either distally or proximally to align with a particular graduation 116 indicating the desired set pressure. In some embodiments, a plurality of longitudinally extending splines 170 may be disposed on the outer surface of the pressure adjuster 140. The plurality of longitudinally extending splines 170 may be advantageous in providing a ridged surface on the pressure adjuster 140 which may enhance for gripping of the pressure adjuster 140 during rotation.

The various embodiments of the pressure-regulating connector described herein including the pressure adjuster 140 are advantageous in allowing the user or other medical professional to adjust the infusion pressure and customize as per patient need. For example, in some embodiments the pressure adjuster may operate on four settings of operation (e.g., setting modes 1, 2, 3, and 4). In particular, a user may use a thumb or other finger to rotate the pressure adjuster so that the indicator 143 is aligned with a desired setting mode. In some embodiments, the pressure adjuster 140 may be rotated and set to setting mode 1 for some of the most sensitive patients, for example patients undergoing chemotherapy. The pressure adjuster 140 may alternatively be rotated and set to setting mode 2 for less sensitive patients, for example pediatric and geriatric patients. Additionally, setting mode 3 may be used for more healthy patients, who are not particularly sensitive to higher pressures. In some embodiments, setting mode 4 may be used when it is desired to bypass the pressure regulating safety mechanism of the connector 100. In some embodiments. Setting mode 4 with no active pressure regulation may be set as the default setting mode. Accordingly, by moving the pressure adjuster 140 proximally or distally, the user can advantageously increase or decrease the pressure of the fluid administered to the patient as desired.

Figures 7A, 7B, 7C, 7D, 7E, 7F:
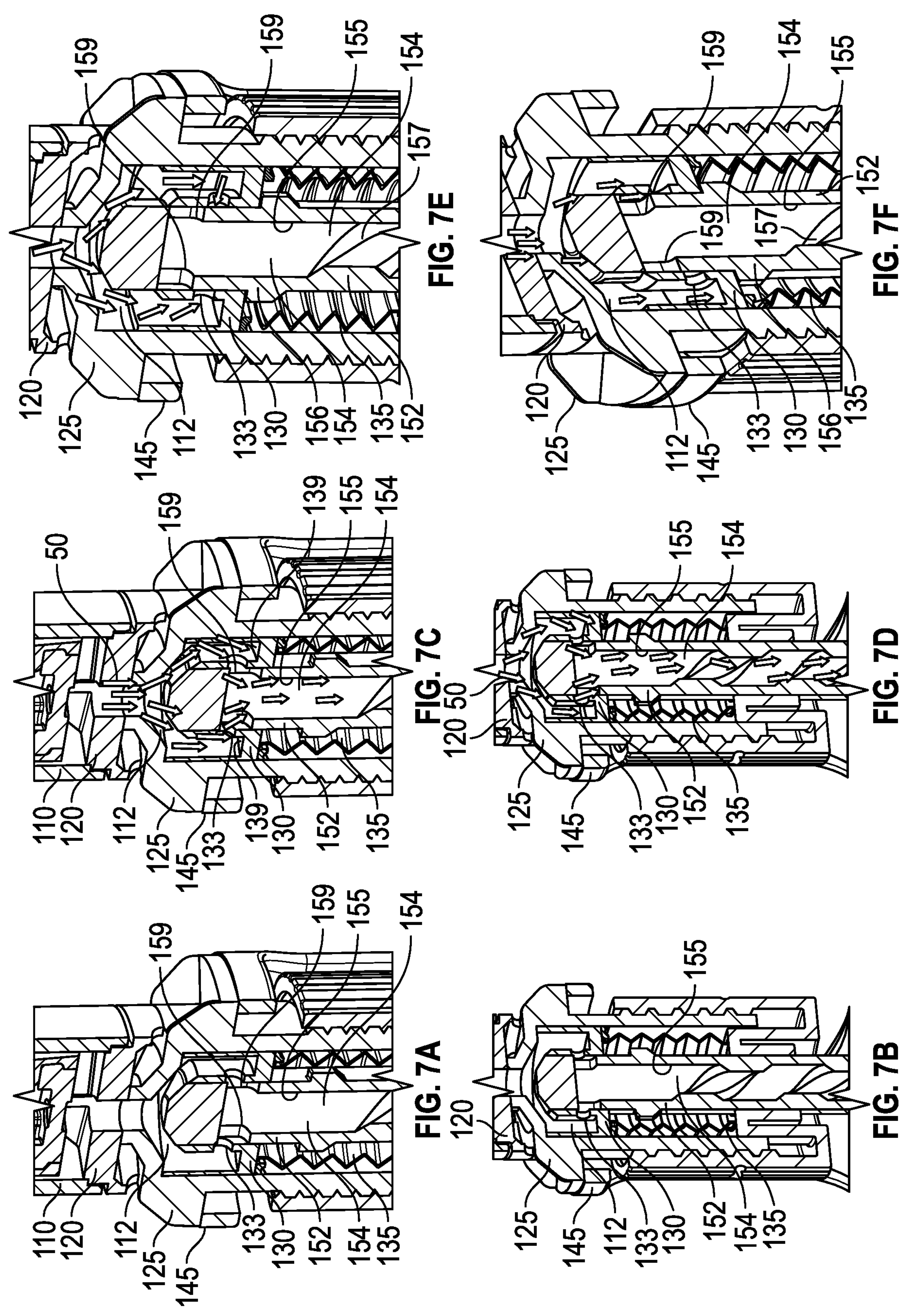
FIGS. 7A and 7B are cross-sectional views of the pressure-regulating connector prior to operation, in accordance with some embodiments of the present disclosure.
FIGS. 7C and 7D are cross-sectional views of the pressure-regulating connector during operation in the open position, in accordance with some embodiments of the present disclosure.
FIGS. 7E and 7F are cross-sectional views of the pressure-regulating connector during operation in the closed position, in accordance with some embodiments of the present disclosure.

The operation of the pressure-regulating connector 100 is described below with reference to FIGS. 7A-7F. FIGS. 7A and 7B are cross-sectional views of the pressure-regulating connector prior to operation, in accordance with some embodiments of the present disclosure. As illustrated in FIGS. 7A and 7B, In the absence of a medical fluid circulating inside the pressure-regulating connector 100, the resilient member 135 maintains the slider 130 in a position corresponding to the proximal-most position of the slider 130.

FIGS. 7C and 7D are cross-sectional views of the pressure-regulating connector during operation in the open position, in accordance with some embodiments of the present disclosure.

When the user pushes the plunger of the medical container (e.g., syringe 10) for infusing the medical fluid, fluid pressure gets built within the syringe 10. Accordingly, a distal pressure is exerted on a floor 139 of the internal compartment 131 of slider 130. This distal pressure displaces or otherwise moves the slider 130 distally, thereby compressing the resilient member 135. As long as the fluid pressure is less than or equal to the predetermined threshold, the slider 130 is maintained by the resilient member 135 in an open position (FIGS. 7C and 7D). In some embodiments, the predetermined pressure threshold corresponds to what is considered safe infusion pressure. For example, the predetermined threshold pressure may be equal to approximately 25 pounds per square inch (psi).

As previously described, and as illustrated in FIGS. 7C and 7D, in the open position, the pair of apertures 133 of the slider 130 may be aligned or at least partially overlap with the pair of cutouts 159 of the fluid channel 152 to allow the medical fluid 50 to flow through the outlet port 169 (illustrated in FIG. 2) via the internal compartment 131 and the fluid channel 152.

FIGS. 7E and 7F are cross-sectional views of the pressure-regulating connector 100 during operation in the closed position, in accordance with some embodiments of the present disclosure. As depicted in FIGS. 7E and 7F, when the fluid pressure exceeds the predetermined threshold for what is considered safe infusion, the distal force exerted on the slider 130 may cause the slider 130 to be further displaced or otherwise moved distally a distance D along the length of the fluid channel 152 towards the second or closed position, illustrated for example in FIG. 6B. For example, the resilient member 135 may further compress to allow the slider 130 to be displaced a second distance to the second or closed position when the medical fluid applies the fluid pressure that is greater than the predetermined threshold or safe infusion. In some embodiments, when the fluid pressure is greater than safe infusion pressure (for example, 25 psi), the slider 130 may travel further distally by further compressing the resilient member 135.

The slider 130 may continue to be displaced further distally by the fluid pressure until the base of the slider 130 abuts against the stop 156 which protrudes radially outward from the outer surface of the fluid channel 152. Accordingly, the slider 130 may be prevented from moving further distally past the second or closed position, as illustrated in FIG. 7B. When the total slider movement or displacement D is equal to approximately 2 millimeters (mm), the slider 130 blocks the fluid from flowing into the fluid channel 152. As previously discussed, in the closed position, the pair of apertures 133 of the slider 130 may not be aligned or may not otherwise overlap with the pair of cutouts 159 such that the inner walls 126 of the slider 130 block fluid connection between the internal compartment 131 of the slider 130 and the pair of cutouts 159 of the fluid channel 152. Accordingly, medical fluid having fluid pressure above the threshold safe amount is trapped inside the slider 130 and cannot flow into the vascular access device. As such, infusion pressure of the medical fluid to the vascular access device may be maintained at or below safe infusion pressures, thereby advantageously preventing issues commonly occurring with currently existing infusion connectors.

When the fluid pressure decreases to a point where it is lower than or equal to the predetermined threshold again, the resilient member 135 may push the slider 130 proximally towards the open position of at least FIGS. 7C and 7D. The inner walls 126 of the slider may move proximally away from the outlet 169, and the pair of apertures 133 and pair of cutouts 159 may again overlap or be at least partially aligned, thereby allowing the medical fluid to again enter the fluid channel 152 via the at least partially aligned pair of apertures 133 and pair of cutouts 159. Accordingly, the medical fluid may then flow through the fluid channel 152, exit the pressure-regulating connector 100, and circulate into the vascular access device.

Figures 8A, 8B:
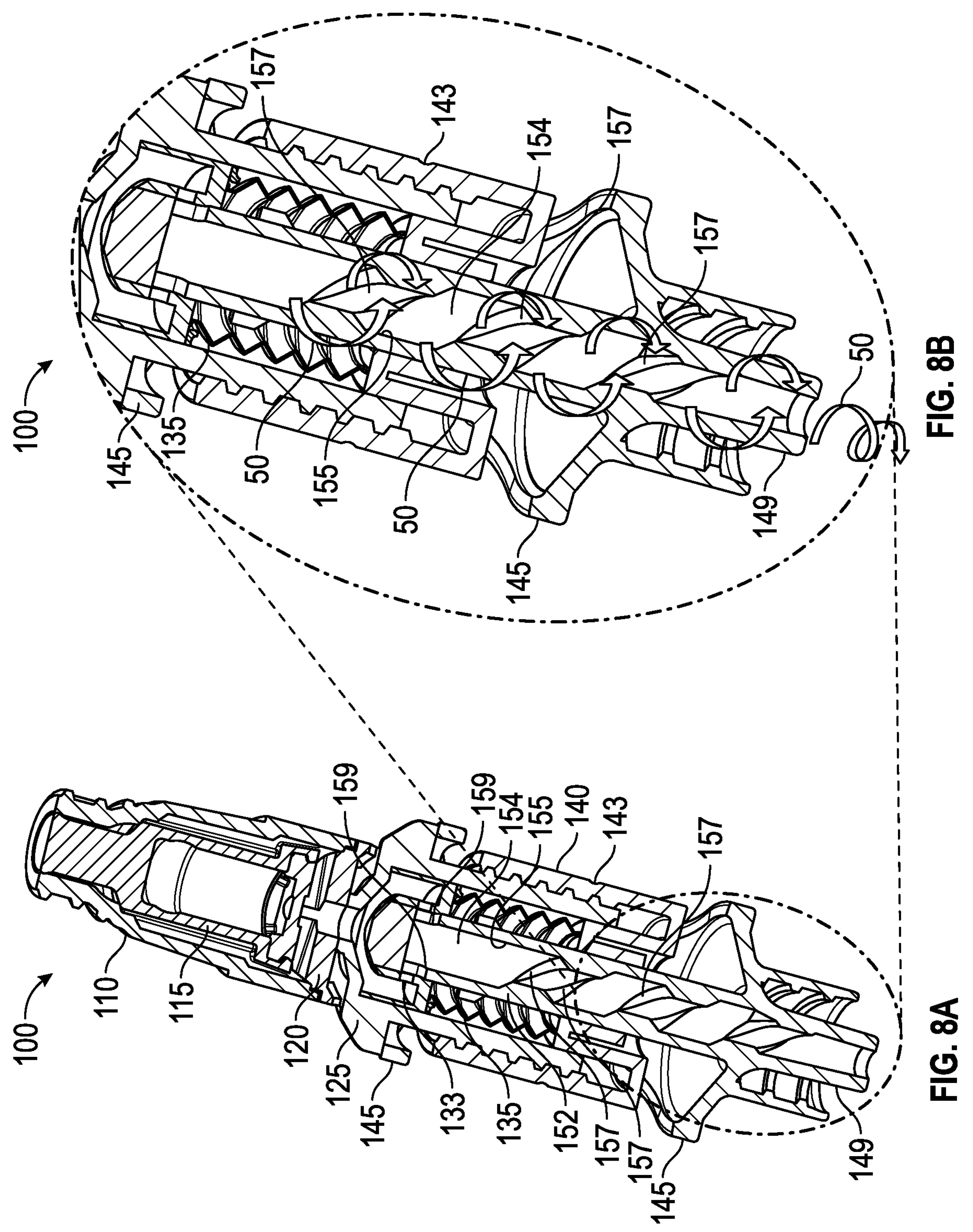
FIG. 8A illustrates a cross-sectional view of the pressure-regulating connector including fluid channel with threaded profile, in accordance with some embodiments of the present disclosure.
FIG. 8B illustrates an enlarged partial cross-sectional view of the pressure-regulating connector of FIG. 8A including fluid channel with threaded profile, in accordance with some embodiments of the present disclosure.

FIG. 8A illustrates a cross-sectional view of the pressure-regulating connector 100 including fluid channel 152 with threaded profile 157, in accordance with some embodiments of the present disclosure. FIG. 8B illustrates an enlarged partial cross-sectional view of the pressure-regulating connector 100 of FIG. 8A including fluid channel 152 with threaded profile 157, in accordance with some embodiments of the present disclosure. According to various embodiments of the present disclosure, the fluid channel 152 may include an inner surface 155 defining a lumen 154 of the fluid channel 152. As illustrated in FIGS. 8A and 8B, the inner surface 155 may have a threaded profile 157 extending at least partially along the inner surface 155. For example, in some embodiments, the threaded profile may include a plurality of helical threads spaced apart from each other. In other embodiments, the threaded profile may include a plurality of circular threads 157 spaced apart from each other. In operation, as the fluid flows through the portion of the lumen 154 having the threaded profile, the threaded profile may cause the fluid to swirl around and create turbulence in the fluid exiting the pressure-regulating connector 100. The pressure regulating connector 100 including the fluid channel 152 with inner surface 155 having a threaded profile 157 is advantageous over currently existing connectors in that the turbulence caused as the medical fluid travels through the portion of the fluid channel 152 having the threaded profile reduces or otherwise eliminates the need for a separate push-pause mechanism as implemented in currently existing connectors.

The pressure-regulating connectors and systems of the various embodiments described herein additionally provide further advantages over currently existing infusion connectors. For example, pressure-regulating connectors and systems described herein provide a pressure control mechanism integrated with a needleless connector, thereby eliminating the need for additional components, and potentially providing a cost savings. Further, the pressure-regulating connectors and systems of the various embodiments described herein having the pressure adjuster allow the user to adjust infusion pressure according to individual or customized patient health conditions. Additionally, the pressure-regulating connectors and systems of the various embodiments described herein may maintain safe infusion pressure by regulating the flow with the reciprocating slider assembly. Furthermore, the pressure-regulating connectors and systems of the various embodiments described herein including the fluid channel with inner surface having threaded profile, which creates turbulent flow, eliminates the need for the push-pause techniques applied by currently existing connectors.

Further advantageously, because the pressure-regulating connectors and systems of the various embodiments incorporate a pressure control mechanisms and pressure selection mechanisms, they advantageously eliminate, or significantly reduce, pain to the patient associated with higher infusion pressures.

Illustration of Subject Technology as Clauses

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 5. The other clauses can be presented in a similar manner.

Clause 1. A connector for connecting a container containing a medical fluid to a vascular access device, the connector including: a housing including a proximal end, a distal end defining an outlet, and an inner surface defining an internal chamber including a fluid channel disposed in the internal chamber, wherein the fluid channel extends from the proximal end to the distal end, and the fluid channel comprises a pair of oppositely positioned cutouts along a length thereof; and a slider disposed and supported in the internal chamber, and sleeved over the fluid channel, the slider including an internal compartment and an aperture through inner walls of the internal compartment, wherein the slider is reciprocally movable between (i) a first position, where the aperture of the slider at least partially overlaps with the pair of cutouts to allow the medical fluid to flow through the outlet, and (ii) a second position where the aperture of the slider is not aligned with the pair of cutouts and the inner walls of the slider block fluid connection between the slider and the fluid channel, and wherein the slider is movable to the first position when the medical fluid applies a fluid pressure less than or equal to a predetermined threshold, and the slider is movable to the second position when the medical fluid applies a fluid pressure greater than the predetermined threshold.

Clause 2. The connector of clause 1, further including a resilient member mounted over the fluid channel and coupled distally to the slider to support the slider within the internal chamber, wherein the resilient member is compressible to allow the slider to (i) move a first distance to the first position when the medical fluid applies the fluid pressure less than or equal to the predetermined threshold, and (ii) move a second distance to the second position when the medical fluid applies a fluid pressure greater than the predetermined threshold.

Clause 3. The connector of clause 2, further including an end cap mounted over the fluid channel at the proximal end, wherein the end cap blocks the medical fluid from entering the fluid channel at the proximal end such that the medical fluid is directed into the internal compartment of the slider.

Clause 4. The connector of clause 2, wherein the first distance is greater than 0 millimeters (mm), but less than 2 mm, and the second distance is equal to 2 mm.

Clause 5. The connector of clause 2, wherein the predetermined threshold is equal to 25 pounds per square inch (psi).

Clause 6. The connector of clause 2, wherein the fluid channel comprises a stop protruding radially outward from an outer surface of the fluid channel, the stop configured to prevent the slider from moving distally past the second position.

Clause 7. The connector of clause 2, wherein the resilient member comprises a bellows extending around an outer surface of the fluid channel.

Clause 8. The connector of clause 2, further including a seal disposed at a base of the slider surrounding the fluid channel to prevent leakage of the medical fluid between the slider and the fluid channel.

Clause 9. The connector of clause 2, further including a cover coupled to the housing surrounding the slider, the fluid channel and the resilient member, and a needleless connector mounted to the cover and fluidly coupled to the slider.

Clause 10. The connector of clause 9, wherein the needleless connector comprises a base plate defining an outlet port of the needleless connector and the cover defines an inlet port at a proximal end thereof, the outlet port and the inlet port fluidly communicating a fluid chamber of the needleless connector with the internal compartment of the slider.

Clause 11. A connector for connecting a container containing a medical fluid to a vascular access device, the connector including: a housing including a proximal end, a distal end defining an outlet, and an inner surface defining an internal chamber including a fluid channel disposed in the internal chamber, wherein the fluid channel extends from the proximal end to the distal end, and the fluid channel comprises an inner surface defining a lumen of the fluid channel, the inner surface including a threaded profile extending at least partially along the inner surface; and a slider disposed and supported in the internal chamber and sleeved over the fluid channel, wherein the slider is reciprocally movable between (i) an open position when the medical fluid applies a fluid pressure less than or equal to a predetermined threshold, and where the slider is fluidly coupled to the fluid channel to allow the medical fluid to flow along the threaded profile to the outlet, and (ii) a closed position when the medical fluid applies a fluid pressure greater than the predetermined threshold, and where fluid connection between the slider and the fluid channel is blocked.

Clause 12. The connector of clause 11, further including a resilient member mounted over the fluid channel and coupled distally to the slider to support the slider within the internal chamber, wherein the resilient member is compressible to allow the slider to reciprocate between the open and closed positions.

Clause 13. The connector of clause 12, wherein threaded profile comprises a plurality of helical threads spaced apart from each other.

Clause 14. The connector of clause 13, wherein: the fluid channel comprises a pair of oppositely positioned cutouts along a length thereof, and the slider comprises an internal compartment and an aperture through inner walls of the internal compartment; and (i) in the open position, the aperture of the slider is axially aligned with the pair of cutouts to allow the medical fluid to flow through the outlet, and (ii) in the closed position, the aperture of the slider is not aligned with the pair of cutouts.

Clause 15. The connector of clause 14, further including a cover coupled to the housing surrounding the slider, the fluid channel and the resilient member, and a needleless connector mounted to the cover and fluidly coupled to the slider.

Clause 16. The connector of clause 15 wherein the needleless connector comprises a base plate defining an outlet port of the needleless connector and the cover defines an inlet port at a proximal end thereof, the outlet port and the inlet port fluidly communicating a fluid chamber of the needleless connector with the internal compartment of the slider.

Clause 17. The connector of clause 12, further including a seal disposed at a base of the slider surrounding the fluid channel to prevent leakage of the medical fluid between the slider and the fluid channel.

Clause 18. A connector for connecting a container containing a medical fluid to a vascular access device, the connector, including: a housing including a proximal end, a distal end defining an outlet, and an inner surface defining an internal chamber including a fluid channel disposed in the internal chamber, wherein the fluid channel extends from the proximal end to the distal end, and the housing further comprises an opening extending through the inner and outer surfaces thereof; a pressure adjuster mounted in the internal chamber and rotatably actuatable via the opening to adjust a pressure of the medical fluid; and a slider disposed and supported in the internal chamber and sleeved over the fluid channel, wherein the slider is reciprocally movable between (i) an open position when the medical fluid applies a fluid pressure less than or equal to a predetermined threshold, and where the slider is fluidly coupled to the fluid channel to allow the medical fluid to flow to the outlet, and (ii) a closed position when the medical fluid applies a fluid pressure greater than the predetermined threshold, and where fluid connection between the slider and the fluid channel is blocked.

Clause 19. The connector of clause 18, further including a resilient member mounted over the fluid channel and coupled distally to the slider to support the slider within the internal chamber, wherein the resilient member is compressible to allow the slider to reciprocate between the open and closed positions.

Clause 20. The connector of clause 19, further including a cover coupled to the housing surrounding the slider, the fluid channel and the resilient member, wherein:

the cover comprises an outer surface having a plurality of engagement features; and the pressure adjuster comprises an inner surface including a plurality of complementary engagement features for coupling to the plurality of engagement features of the cover.

Clause 21. The connector of clause 20, wherein the outer surface of the housing comprises a plurality of graduations, and the pressure adjuster further comprises an indicator disposed around at least a portion of the outer surface of the pressure adjuster, and when the pressure adjuster is rotated to adjust the fluid pressure, the plurality of engagement features of the pressure adjuster and the cover engage and interconnect to rotate the pressure adjuster and translate the indicator to align with a graduation of the plurality of graduations.

Clause 22. The connector of clause 21, wherein the plurality of graduations represent various fluid pressures.

Clause 23. The connector of clause 21, wherein the outer surface of the pressure adjust further comprises a plurality of longitudinally extending splines for gripping the pressure adjuster.

Clause 24. The connector of clause 21, further including a seal disposed at a base of the slider surrounding the fluid channel to prevent leakage of the medical fluid between the slider and the fluid channel.

Clause 25. The connector of clause 21, further including a cover coupled to the housing surrounding the slider, the fluid channel and the resilient member, and a needleless connector mounted to the cover and fluidly coupled to the slider.

Clause 26. The connector of clause 25 wherein the needleless connector comprises a base plate defining an outlet port of the needleless connector and the cover defines an inlet port at a proximal end thereof, the outlet port and the inlet port fluidly communicating a fluid chamber of the needleless connector with an internal compartment of the slider.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean “one and only one” unless specifically so stated, but rather “one or more.” Unless specifically stated otherwise, the term “some” refers to one or more. Pronouns in the masculine (e.g., his) include the feminine and neuter gender (e.g., her and its) and vice versa. Headings and subheadings, if any, are used for convenience only and do not limit the invention.

The word “exemplary” is used herein to mean “serving as an example or illustration.” Any aspect or design described herein as “exemplary” is not necessarily to be construed as preferred or advantageous over other aspects or designs. In one aspect, various alternative configurations and operations described herein may be considered to be at least equivalent.

As used herein, the phrase “at least one of” preceding a series of items, with the term “or” to separate any of the items, modifies the list as a whole, rather than each item of the list. The phrase “at least one of” does not require selection of at least one item; rather, the phrase allows a meaning that includes at least one of any one of the items, and/or at least one of any combination of the items, and/or at least one of each of the items. By way of example, the phrase “at least one of A, B, or C” may refer to: only A, only B, or only C; or any combination of A, B, and C.

A phrase such as an “aspect” does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an “embodiment” does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a “configuration” does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, or operations in the processes or methods disclosed are illustrations of exemplary approaches. Based upon implementation preferences or scenarios, it is understood that the specific order or hierarchy of steps, operations or processes may be rearranged. Some of the steps, operations or processes may be performed simultaneously. In some implementation preferences or scenarios, certain operations may or may not be performed. Some or all of the steps, operations, or processes may be performed automatically, without the intervention of a user. The accompanying method claims present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein but are to be accorded the full scope consistent with the language of the claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A connector for connecting a container containing a medical fluid to a vascular access device, the connector comprising:

a housing comprising a proximal end, a distal end defining an outlet, and an inner surface defining an internal chamber comprising a fluid channel disposed in the internal chamber, wherein the fluid channel extends from the proximal end to the distal end, and the fluid channel comprises a pair of oppositely positioned cutouts along a length thereof; and a slider disposed and supported in the internal chamber, and sleeved over the fluid channel, the slider comprising an inner wall, an outer wall, an internal compartment defined between the inner wall and the outer wall, and an aperture through the inner wall, wherein the internal compartment is configured to receive the medical fluid to move the slider between (i) a first position, where the aperture of the slider at least partially overlaps with the pair of cutouts to allow the medical fluid to flow through the outlet, and (ii) a second position where the aperture of the slider is not aligned with the pair of cutouts and the inner wall of the slider block fluid connection between the slider and the fluid channel, and wherein the slider is movable to the first position when the medical fluid applies a fluid pressure less than or equal to a predetermined threshold, and the slider is movable to the second position when the medical fluid applies a fluid pressure greater than the predetermined threshold, wherein the slider is movable while maintaining the blocked fluid connection between the slider and the fluid channel in the second position.

2. The connector of claim 1, further comprising a resilient member mounted over the fluid channel and coupled distally to the slider to support the slider within the internal chamber, wherein the resilient member is compressible to allow the slider to (i) move a first distance to the first position when the medical fluid applies the fluid pressure less than or equal to the predetermined threshold, and (ii) move a second distance to the second position when the medical fluid applies a fluid pressure greater than the predetermined threshold.

3. The connector of claim 2, further comprising an end cap mounted over the fluid channel at the proximal end, wherein the end cap blocks the medical fluid from entering the fluid channel at the proximal end such that the medical fluid is directed into the internal compartment of the slider.

4. The connector of claim 2, wherein the first distance is greater than 0 millimeters (mm), but less than 2 mm, and the second distance is equal to 2 mm.

5. The connector of claim 2, wherein the predetermined threshold is equal to 25 pounds per square inch (psi).

6. The connector of claim 2, wherein the fluid channel comprises a stop protruding radially outward from an outer surface of the fluid channel, the stop configured to abut against a base of the slider in a stopped position to prevent the slider from moving distally past the second position, wherein the stopped position is distally past the second position.

7. The connector of claim 2, wherein the resilient member comprises bellows extending around an outer surface of the fluid channel.

8. The connector of claim 2, further comprising a seal disposed at a base of the slider surrounding the fluid channel to prevent leakage of the medical fluid between the slider and the fluid channel.

9. The connector of claim 2, further comprising a cover coupled to the housing surrounding the slider, the fluid channel and the resilient member, and a needleless connector mounted to the cover and fluidly coupled to the slider.

10. The connector of claim 9, wherein the needleless connector comprises a base plate defining an outlet port of the needleless connector and the cover defines an inlet port at a proximal end thereof, the outlet port and the inlet port fluidly communicating a fluid chamber of the needleless connector with the internal compartment of the slider.

11. A connector for connecting a container containing a medical fluid to a vascular access device, the connector comprising:

a housing comprising a proximal end, a distal end defining an outlet, and an inner surface defining an internal chamber comprising a fluid channel disposed in the internal chamber, wherein the fluid channel extends from the proximal end to the distal end, and the fluid channel comprises an inner surface defining a lumen of the fluid channel, the inner surface comprising a threaded profile extending at least partially along the inner surface; and a slider disposed and supported in the internal chamber and sleeved over the fluid channel, the slider comprising an inner wall, an outer wall, and an internal compartment defined between the inner wall and the outer wall, and an aperture through the inner wall wherein the slider is reciprocally movable between (i) an open position when the medical fluid applies a fluid pressure less than or equal to a predetermined threshold to the internal compartment, and where the slider is fluidly coupled to the fluid channel to allow the medical fluid to flow along the threaded profile to the outlet, and (ii) a closed position when the medical fluid applies a fluid pressure greater than the predetermined threshold to the internal compartment, and where fluid connection between the slider and the fluid channel is blocked, wherein the slider is movable while maintaining the blocked fluid connection between the slider and the fluid channel in the closed position.

12. The connector of claim 11, further comprising a resilient member mounted over the fluid channel and coupled distally to the slider to support the slider within the internal chamber, wherein the resilient member is compressible to allow the slider to reciprocate between the open and closed positions.

13. The connector of claim 11, wherein threaded profile comprises a plurality of helical threads spaced apart from each other.

14. The connector of claim 11, wherein:

the fluid channel comprises a pair of oppositely positioned cutouts along a length thereof; and (i) in the open position, the aperture of the slider is axially aligned with the pair of cutouts to allow the medical fluid to flow through the outlet, and (ii) in the closed position, the aperture of the slider is not aligned with the pair of cutouts.

15. The connector of claim 12, further comprising a cover coupled to the housing surrounding the slider, the fluid channel, and the resilient member, and a needleless connector mounted to the cover and fluidly coupled to the slider.

16. The connector of claim 15 wherein the needleless connector comprises a base plate defining an outlet port of the needleless connector and the cover defines an inlet port at a proximal end thereof, the outlet port and the inlet port fluidly communicating a fluid chamber of the needleless connector with the internal compartment of the slider.

17. The connector of claim 11, further comprising a seal disposed at a base of the slider surrounding the fluid channel to prevent leakage of the medical fluid between the slider and the fluid channel.

18. A connector for connecting a container containing a medical fluid to a vascular access device, the connector, comprising:

a housing comprising a proximal end, a distal end defining an outlet, an outer surface, and an inner surface defining an internal chamber comprising a fluid channel disposed in the internal chamber, wherein the fluid channel extends from the proximal end to the distal end, and the housing further comprises an opening extending through the inner and outer surfaces thereof;

a pressure adjuster mounted in the internal chamber and rotatably actuatable via the opening to adjust a pressure of the medical fluid; and a slider disposed and supported in the internal chamber and sleeved over the fluid channel, the slider comprising an inner wall, an outer wall, and an internal compartment defined between the inner wall and the outer wall, and an aperture through the inner wall wherein the internal compartment is configured to receive the medical fluid to move the slider between (i) an open position when the medical fluid applies a fluid pressure less than or equal to a predetermined threshold, and where the slider is fluidly coupled to the fluid channel to allow the medical fluid to flow to the outlet, and (ii) a closed position when the medical fluid applies a fluid pressure greater than the predetermined threshold, and where fluid connection between the slider and the fluid channel is blocked, wherein the slider is movable while maintaining the blocked fluid connection between the slider and the fluid channel in the closed position.

19. The connector of claim 18, further comprising a resilient member mounted over the fluid channel and coupled distally to the slider to support the slider within the internal chamber, wherein the resilient member is compressible to allow the slider to reciprocate between the open and closed positions.

20. The connector of claim 19, further comprising a cover coupled to the housing surrounding the slider, the fluid channel, and the resilient member, wherein:

the cover comprises an outer surface having a plurality of engagement features; and the pressure adjuster comprises an inner surface including a plurality of complementary engagement features for coupling to the plurality of engagement features of the cover.

21. The connector of claim 20, wherein the outer surface of the housing comprises a plurality of graduations, and the pressure adjuster further comprises an indicator disposed around at least a portion of an outer surface of the pressure adjuster, and when the pressure adjuster is rotated to adjust the fluid pressure, the plurality of engagement features of the pressure adjuster and the cover engage and interconnect to rotate the pressure adjuster and translate the indicator to align with a graduation of the plurality of graduations.

22. The connector of claim 21, wherein the plurality of graduations represent various fluid pressures.

23. The connector of claim 21, wherein the outer surface of the pressure adjust further comprises a plurality of longitudinally extending splines for gripping the pressure adjuster.

24. The connector of claim 18, further comprising a seal disposed at a base of the slider surrounding the fluid channel to prevent leakage of the medical fluid between the slider and the fluid channel.

25. The connector of claim 18, further comprising a cover coupled to the housing surrounding the slider, the fluid channel, and the resilient member, and a needleless connector mounted to the cover and fluidly coupled to the slider.

26. The connector of claim 25 wherein the needleless connector comprises a base plate defining an outlet port of the needleless connector and the cover defines an inlet port at a proximal end thereof, the outlet port and the inlet port fluidly communicating a fluid chamber of the needleless connector with an internal compartment of the slider.

* * * * *